(12) United States Patent
Aghazadeh

(10) Patent No.: US 9,375,178 B2
(45) Date of Patent: Jun. 28, 2016

(54) SYSTEMS AND METHODS FOR ALIGNING A MEDICAL DEVICE WITH A PELVIC AXIS

(71) Applicant: ARTHROMEDA, INC., Ayer, MA (US)

(72) Inventor: Mehran S. Aghazadeh, Newton, MA (US)

(73) Assignee: ARTHROMEDA, INC., Ayer, MA (US)

( * ) Notice: Subject to any disclaimer, the term of this patent is extended or adjusted under 35 U.S.C. 154(b) by 0 days.

(21) Appl. No.: 14/331,149

(22) Filed: Jul. 14, 2014

(65) Prior Publication Data
US 2015/0018719 A1 Jan. 15, 2015

Related U.S. Application Data

(60) Provisional application No. 61/845,523, filed on Jul. 12, 2013.

(51) Int. Cl.
A61B 17/58 (2006.01)
A61B 17/60 (2006.01)
A61F 2/00 (2006.01)
A61B 5/00 (2006.01)
A61B 5/107 (2006.01)

(52) U.S. Cl.
CPC ............ *A61B 5/4851* (2013.01); *A61B 5/1071* (2013.01); *A61B 5/6847* (2013.01); *A61B 5/6878* (2013.01)

(58) Field of Classification Search
None
See application file for complete search history.

(56) References Cited

U.S. PATENT DOCUMENTS

| 5,601,550 | A | 2/1997 | Esser |
| 6,395,005 | B1 | 5/2002 | Lovell |
| 2011/0087230 | A1 | 4/2011 | Graf et al. |
| 2014/0052149 | A1 | 2/2014 | van der Walt et al. |
| 2014/0330281 | A1* | 11/2014 | Aghazadeh ........... A61F 2/4609 606/102 |

FOREIGN PATENT DOCUMENTS

| WO | 2006/109983 A1 | 10/2006 |
| WO | 2012/125795 A2 | 9/2012 |
| WO | 2013/049534 A1 | 4/2013 |

OTHER PUBLICATIONS

International Search Report and Written Opinion for Application No. PCT/US2014/046566 mailed Dec. 22, 2014 (23 pages).

* cited by examiner

*Primary Examiner* — Sameh Boles
(74) *Attorney, Agent, or Firm* — Nutter McClennen & Fish LLP

(57) ABSTRACT

One embodiment of a system described herein can include an axis guide for placement over a patient's right and left ASIS and at least two guides attachable to the axis guide to provide a through hole that is perpendicular to the axis guide. The system can further include at least two probes that can fit through the through holes and extend beyond an end of the axis guide by a predetermined distance, as well as at least two bone engaging pins that fit through the through holes. When the guides are assembled to the axis guide and the probes are assembled to the guides, the axis guide can be placed so that the probes contact the patient's pelvis and the probes can be replaced by the pins to mount the pins to the patient's pelvis in a known orientation.

8 Claims, 19 Drawing Sheets

232'   234'

SYSTEMS AND METHODS FOR ALIGNING A MEDICAL DEVICE WITH A PELVIC AXIS

CROSS-REFERENCE TO RELATED APPLICATION

This application claims the benefit of U.S. Provisional Application No. 61/845,523, filed Jul. 12, 2013.

FIELD

This application relates generally to surgical procedures and, more particularly, to instruments and methods utilized in hip prosthetic surgeries.

BACKGROUND

Successful hip prosthetic surgery requires precise intra-operative placement and positioning of replacement structures as implants within the patient such that the in vivo function of the reconstructed joint is optimized biomechanically and biologically. For the surgeon, it is necessary to ensure that the replacement structural components are implanted correctly and function in situ properly in order to avoid intraoperative and post-operative complications, as well as to ensure a long-lasting action and use for the implanted prosthesis.

Important parameters for achieving a successful hip arthroplasty procedure include: (1) the position angles of the cup implanted in the patient's pelvis; (2) the position angle of the stem implanted in the patient's femur; and (3) the longitudinal placement of the stem.

A malpositioned hip prosthesis will not adequately restore the joint's biomechanics, will not function properly, and is at increased risk of intra-operative and post-operative complications. Such complications can include, without limitation, dislocation, impingement, fracture, implant failure, aseptic loosening, and subsidence. A malpositioned prosthetic implant is particularly susceptible to dislocation and early loosening because the prosthesis will not be well fitted or supported within the host's native bone.

One problem routinely faced by surgeons today concerning human hip replacement procedures is how to achieve proper acetabular prosthetic implant alignment. It is generally agreed among orthopedic surgeons that the ideal anatomic position (for most patients) for positioning the acetabular prosthetic implant within the native bone of the host's hip is at 45° (degrees) of inclination.

A second important angle is the angle of forward flexion, which ideally is at 20° (degrees). More recent advanced techniques emphasize "combined anteversion" of the reconstructed hip, rather than the cup's absolute angle of forward flexion. Combined anteversion is the sum of the angle of forward flexion of the cup plus the angle of anteversion of the stem. Since there is limited space for changing the stem's angle of anteversion, adjusting the position of the cup to that of the stem is critical to improving stability of the reconstructed hip and reducing impingement.

However, precise measurement of these specific angles, and therefore proper placement of the prostheses, has been difficult to achieve, mostly because two of these angles are relative to the patient's pelvis and the patient is covered by sterile surgical drapes during the course of the hip replacement operation. It also has not been possible to monitor any change in position of the patient's pelvis that can occur after draping the patient for the surgery.

SUMMARY

The present invention generally provides an apparatus and method for placing a sensor on a patient in a known angular relationship to the patient's pelvic axis. By accurately placing such a sensor on the patient, the orientation of the patient's pelvic axis can be monitored and tracked throughout a procedure (even if there is movement after initial staging of the patient) and the information can be used to accurately and precisely implant an acetabular cup implant at a desired angle.

In one aspect, a system for providing pins in a patient's pelvis for attaching an orientation sensor in a known relationship to the patient's pelvic axis is provided that includes an axis guide for placement over a patient's right and left Anterior Superior Iliac Spine (ASIS) having a surgical side and a non-surgical side, where the surgical side includes at least two guide mating holes. The system can further include at least two guides attachable to the guide mating holes so as to provide a through hole that is perpendicular to the axis guide, and at least two probes, where each probe fits through the through holes and has a locking feature that engages a feature on the guides that locks the axial position of the probe so that it extends by a predetermined distance beyond the end of the axis guide when assembled. The system can also include at least two bone engaging pins, where each bone engaging pin fits through the through holes and has a bone engaging feature on its distal end. Further, when the guides are assembled to the axis guide and the probes are assembled to the guides, and the axis guide can be placed so that the probes contact the patient's pelvis and the probes can be replaced by the pins so as to mount the pins to the patient's pelvis in a direction that is normal to the patient's coronal plane.

The systems and methods described herein can have a number of additional features or variations, all of which are considered within the scope of the present invention. For example, in some embodiments, the non surgical side of the axis guide can include two guide mating holes, and the system can include two further guides and two further probes. In other embodiments, the guide mating holes can be arranged in a square pattern.

In still other embodiments, the axis guide can include a plurality of selectable guide mating holes for placement of a single guide. In addition, the probes can extend beyond the axis guide by between about 10 mm and about 60 millimeters when the guides are assembled to the axis guide and the probes are assembled to the guides.

In certain embodiments, the system can further include a tilt sensor mountable to the pins in a known orientation with respect to the patient's pelvic axis. Further, in some embodiments the tilt sensor can include a transmission element and the system can include a computing device having a graphical user interface that provides visual guidance as to the orientation of the patient's pelvic axis.

In another aspect, a method for providing pins in a patient's pelvis for attaching an orientation sensor in a known relationship to the patient's pelvic axis is provided that includes placing over a patient's right and left ASIS an axis guide having a surgical side and a non-surgical side, the surgical side including at least two guides so as to provide a through hole that is perpendicular to the axis guide. The method can further include fitting probes through the through holes and applying a locking feature on the probes that engages a feature on the guides and locks the axial position of the probes so that the probes extend by a predetermined distance beyond the end of the axis guide when assembled. The method can also include removing at least one probe from a through hole, preparing the patient's pelvis to accept a bone engaging pin through the through hole, and engaging a bone engaging pin to the patient's pelvis through the through hole in a direction that is normal to the patient's coronal plane.

In some embodiments, the method can further include removing a further probe from a further through hole, preparing the patient's pelvis to accept a bone engaging pin through the further through hole, and engaging a bone engaging pin to the patient's pelvis through the through hole in a direction that is normal to the patient's coronal plane. In certain embodiments, the bone engaging pins can be engaged to the patient's pelvis so as to define a plane that is parallel to the patient's sagittal plane.

In still other embodiments, the method can further include mounting a tilt sensor to the bone engaging pins in a known orientation with respect to the patient's pelvic axis. In some embodiments, the tilt sensor can be mounted so that it is parallel to the patient's coronal plane.

In another aspect, a system for providing pins in a patient's pelvis for attaching an orientation sensor in a known relationship to the patient's pelvic axis is provided that includes an axis guide for placement over a patient's right and left ASIS having a surgical side and a non-surgical side, the surgical side including at least two guide holes that are perpendicular to the axis guide. The system further includes at least two probes, where each probe fits through the guide holes and has a locking feature that engages a feature on the axis guide that locks the axial position of the probe so that it extends by a predetermined distance beyond the end of the axis guide when assembled. The system also includes at least two bone engaging pins, where each bone engaging pin fits through the guide holes and has a bone engaging feature on its distal end. Further, when the probes are assembled to the axis guide, and the axis guide is placed so that the probes contact the patient's pelvis, the probes can be replaced by the pins so as to mount the pins to the patient's pelvis in a direction that is normal to the patient's coronal plane.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The invention includes a novel apparatus, as well as a unique methodology and system, to place a sensor on a patient in a known angular relationship with the pelvic axis in order to provide measurements that allow a surgeon to implant an acetabular cup at a desired angle, including when there is movement of the patient during surgery.

The invention can be used with the systems and methods of International Publication No. WO2013/049534, which is hereby incorporated in its entirety as if its full contents were repeated here. Those systems and methods provide an intra-operative surgical positioning assessment and angle determination made by anatomic alignment. The method and system determine the patient's true pelvic position/tilt by using the geometric planes as anatomical reference planes, i.e., alignment and angles are measured relative to the true features of the patient, not just to, for example, the operating table. The method and system provide precise information about the angles of inclination and forward flexion of the native bony acetabulum and prosthesis for proper implantation. These measurements and calculations are made in true relationship to the patient's pelvis and body axis during the time when the surgeon is preparing the host bone and handling the prosthesis and is inserting it into the host's native bone structure.

Figure 4:
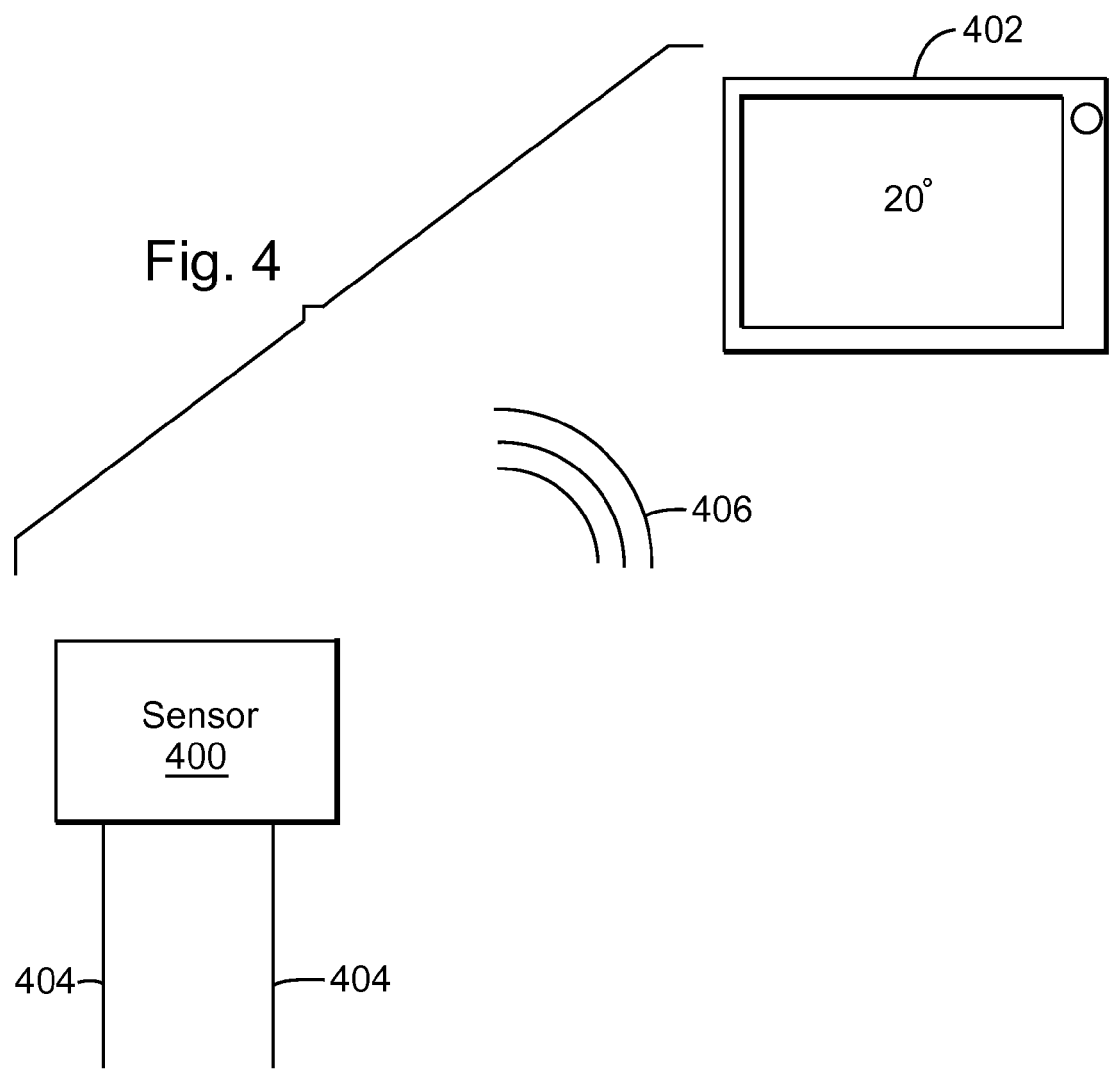
FIG. 4 illustrates one embodiment of a sensor communicating orientation information to a digital display.

As shown in FIG. 4, the measuring sensor units 400 can be inexpensive, highly accurate, digital components able to communicate with a special software program running on a computer processor, personal computer (PC), or hand-held electronic device (e.g., smartphone or electronic tablet), to accurately determine the pelvic tilt. The determination of these angles can also be seen and read by the surgeon via a portable digital visual display 402, thereby removing the need for a PC. In one embodiment, the measuring system continuously monitors the patient's pelvic position, and as a consequence of this capability, the surgeon can effectively ensure an accurate angular placement of the acetabular prosthesis within the patient's native bone. The result will be optimum functionality of the joint and patient satisfaction following surgery.

In particular, an electronic position sensor 400 can be used that is capable of sensing its orientation in 3-dimensional space and transmitting the information to the computer processor. It can be attached to the patient's pelvis (e.g., via pins 404, as described below) and can transmit the position angles of the pelvis to a computer processor and application software. The position sensors used herein can have at least one orientation sensor and at least one transmitter. The transmitter can be any of a variety of types used to transmit information, preferably wirelessly (as shown schematically at 406 in FIG. 4), to a computer or tablet. In one embodiment, the sensors can include a BLUETOOTH transceiver. The orientation sensors 400 preferably specify the tilt of the sensor with respect to orthogonal axes (such as x-y-z axes) and heading with respect to an external field. In exemplary embodiments, accelerometers can be used to determine tilt and a magnetometer can be used to specify orientation with respect to natural or man-made magnetic fields.

The determination of these angles can also be seen and read by the surgeon via a portable digital visual display 402, thereby removing the need for a PC. In one embodiment, the measuring system can continuously monitor the position of the patient's lower limb, and as a consequence of this capability, the surgeon can effectively ensure an accurate angular placement of the cutting instruments in order to prepare the host's native bone and restore the appropriate alignment of leg. This can result in optimum functionality of the joint and patient satisfaction following surgery.

Figure 1:
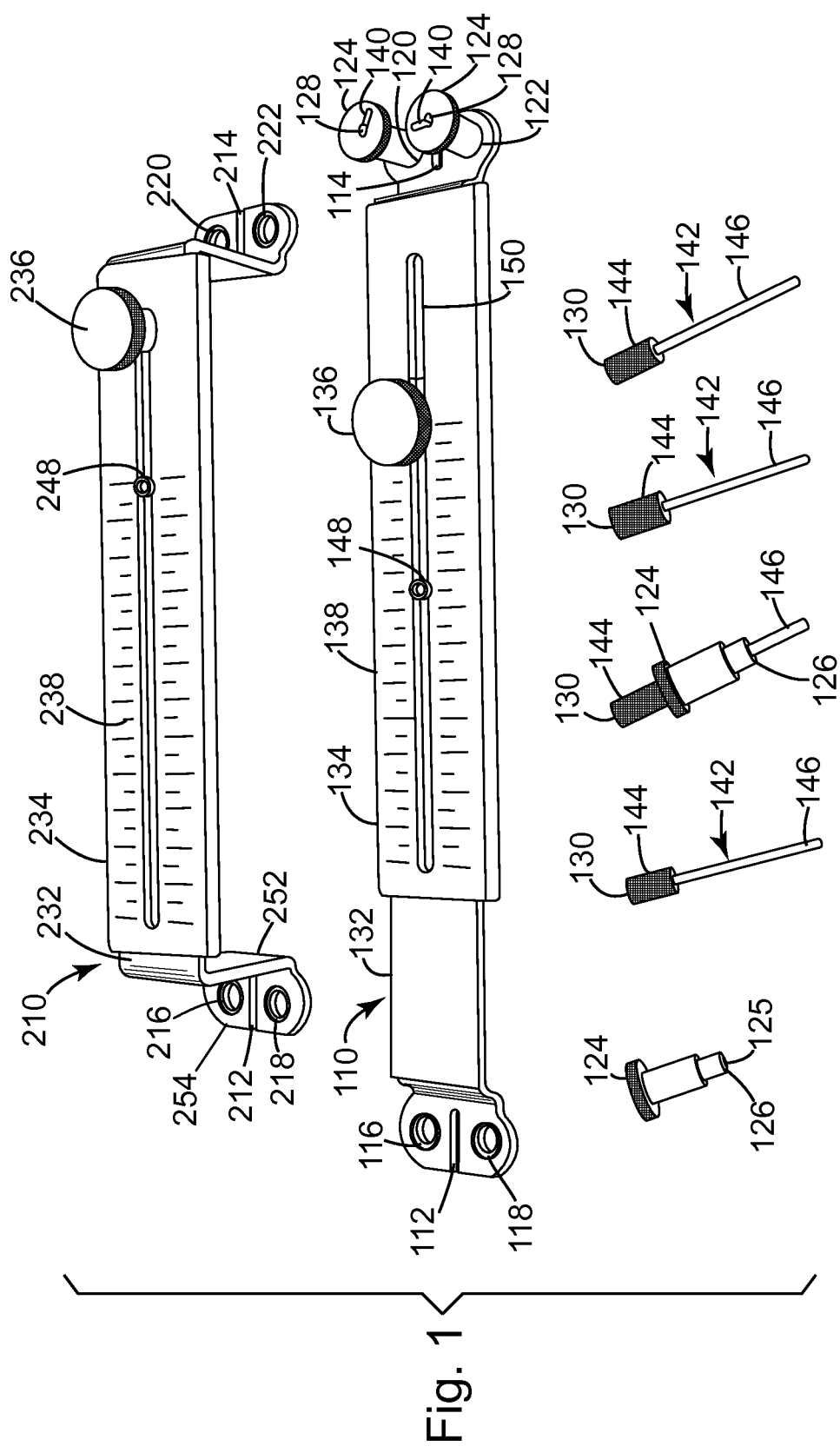
FIG. 1 illustrates one embodiment of a system for placing pins in a patient's pelvis in a known orientation with respect to the patient's pelvic axis.
Figure 2:
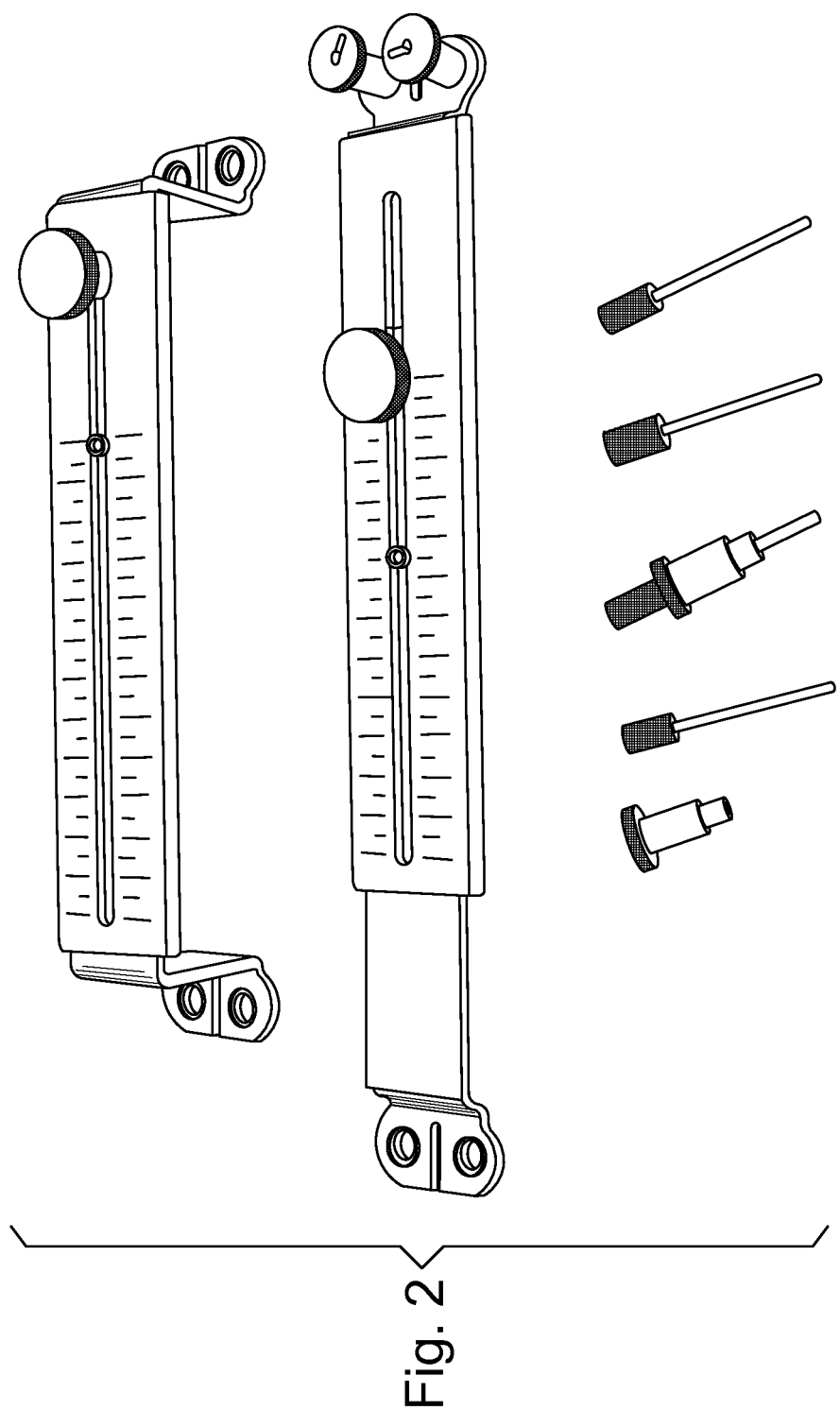
FIG. 2 illustrates the system of FIG. 1 from a different angle.
Figure 6:
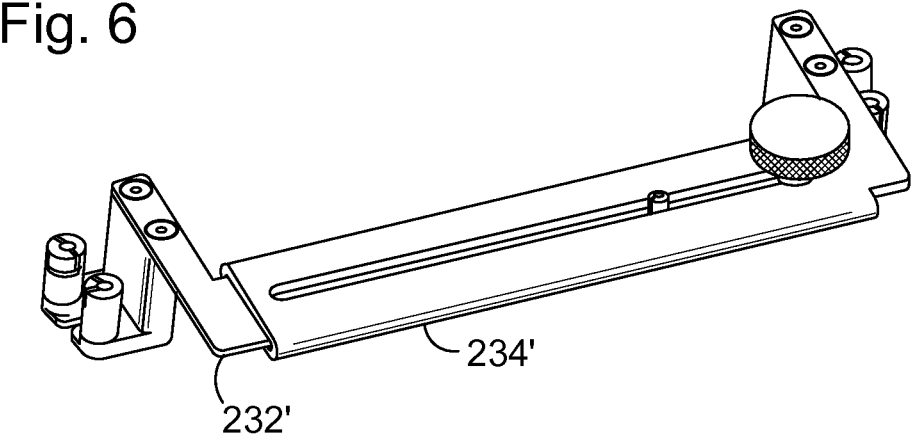
FIG. 6 illustrates an alternative embodiment of a an axis guide.
Figure 7:
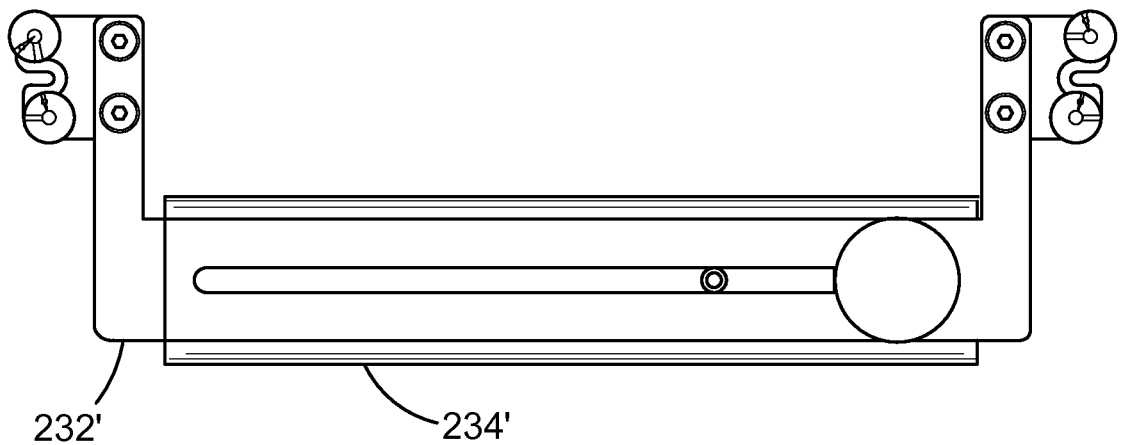
FIG. 7 illustrates a top view of the axis guide of FIG. 6.

The present invention relates to a system and method for placing a sensor on a patient's pelvis in a known orientation with respect to the patent's pelvic axis. An embodiment of the invention is illustrated in FIGS. 1 and 2. These figures include two embodiments of an axis guide 110, 210 that is a rigid bar that serves as a structure for determining position and angles for attaching electronic sensor to the native bony pelvis of the patient. In one embodiment, the axis guide 110 is relatively flat, while in the other embodiment, the axis guide 210 is designed with a vertical offset 252 to accommodate patients for whom the region between the medial and lateral Anterior Superior Iliac Spine (ASIS) is not flat. In another embodiment, illustrated in FIGS. 6 and 7, the sliding midsections 232', 234' of the axis guide are offset inferiorly so as to locate below the patient's abdomen. In still further embodiments, the vertical offset portions can be modular and can be detached from midsections 232 and 234, as shown in FIGS. 6 and 7, so that the size of the vertical offset can be selected based on the patient. In still further embodiments, foot sections 254 can also be modular and detachable from the axis guide. This can allow the foot sections to be replaced with different guide alignments, as discussed below. Because of the similarities between the axis guides 110, 210 (as well as the axis guides illustrated in FIGS. 6-24), only the flatter axis guide 110 will be described below. However, it should be understood that each "100" numbered element on the axis guide 110 corresponds to a "200" numbered element on the axis guide 210, as well as to similar features on the other axis guides.

In one embodiment, the axis guide 110 can be a rigid bar having fixed length, width and depth dimensions, said bar being formed of resilient material which is constructed and arranged so that it can be positioned in, or placed to lie parallel to, the patient's pelvic axis by the surgeon. The axis guide can, but need not necessarily, be made of material that can be sterilized.

In a further embodiment, the axis guide 110 can include two rigid bars 132, 134 slidably connected to each other so as to create a single unit with adjustable length. The bars can have fixed width and depth dimensions and can be formed from resilient materials such as stainless steel. The adjustable length axis guide can be constructed and arranged so that it can be positioned in, or placed to lie parallel to, the patient's pelvic axis by the surgeon. The adjustable length of the axis guide can be designed to accommodate different sizes of pelvis. There can be a releasable locking mechanism 136 in the mid section of the adjustable length axis guide. A length of the axis bar can be adjusted when the locking mechanism is released. Once engaged, the locking mechanism can keep the length constant. In the illustrated embodiments, the locking mechanism 136 is shown including a thumbscrew 1002 (see FIG. 10) having a knurled surface (e.g., in FIGS. 1-8) or other gripping surface/shape (e.g., in FIGS. 9, 10, 20, and 21) that can be selectively tightened onto a threaded protrusion (not shown) formed on the rigid bar 132 that extends through a slot 150 formed in the rigid bar 134. The tightening of the thumbscrew onto the threaded protrusion can compress the rigid bars 123, 134 together, thereby preventing relative movement therebetween.

Figure 3:
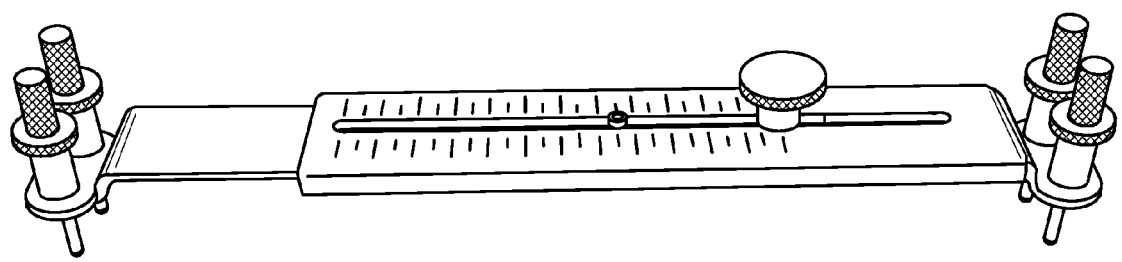
FIG. 3 illustrates the system of FIG. 1 in an assembled configuration.

In the illustrated embodiment, a physical measuring apparatus 138 is integral to the axis guide 110 and indicates the distance between guides on each end. For example, as shown in FIGS. 1-3, the distance can be read off the ruler at a point 148 indicated on, or set by the end of, the other bar. In one embodiment, the ruler is calibrated in millimeters. This distance read off the measuring apparatus is equal to the distance between right and left ASIS in the patient. That is, the measuring apparatus 138 can be calibrated to indicate the distance between lines that extend through the centers of the threaded apertures 116, 118 and 120, 122.

There is an additional slot 112, 114 formed at each end of the axis guide 110 in the foot section 254 which can be used for visualizing and properly placing the axis guide upon marked anatomic spots made by the surgeon on the skin of the patient (as described in more detail below).

As mentioned above, the axis guide 110 can also have threaded apertures 116, 118, 120, 122 lying adjacent to the slot 112, 114 at each end of the axis guide 110 to receive threaded guides 124. The guides 124 can be placed perpendicular to a patient's pelvic axis and parallel to each other, and they can identify the proper place for attaching a sensor to the patient's pelvis.

The guides 124 can be cylinder-shaped articles made of material compatible for use with the axis guide 110. As illustrated in FIGS. 1-3, the guides 124 can have proximal gripping features, in this case, a raised knurled surface, so that the guides can be screwed into the threaded apertures by hand. The guides 124 can have tool engagement surfaces along with, or in place of, the gripping surfaces. In one embodiment, the guides 124 can be made of the same material as the axis guide 110. The guides 124 can be, on their outer aspect, threaded at one end 126 such that they can be introduced into the threaded apertures 116, 118, 120, 122 of the axis guide at 90° angles. Each guide 124 can have an inner through hole 128 that can have an inner diameter just large enough to allow passage of a securing pin (e.g., pin 404 in FIG. 4) so as to permit free rotation of the securing pin with substantially no friction or play.

Guides 124 can also have a keyhole slot 140. This slot 140 can be sized to receive a locking element 142 on a probe 130.

Probes 130 can be similar, at least on a distal portion, to the pins that are inserted through the guide for attachment to the patient. The probes 130, however, can be intended for temporary use to properly position the alignment guide 110. Each illustrated probe 130 can have a proximal gripping surface 144, and a probe pin 146 extending distally from the gripping surface. The probe pin can have a diameter such that it fits through the inner through hole in the guide 124 with substantially no friction or play so that it may be rotated, but remains perpendicular to the axis guide 110 as desired. The probe pin 146 can have a length such that, when the probe pin 146 is placed into the inner through hole 128 of the guide 124, the locking element 142 slides into the keyhole slot 140. The probe 130 can then be turned, with the locking element following a transverse slot below the gripping surface, to axially lock the probe within the guide. In this configuration, the probes 130 can extend a predetermined distance beyond a distal end of the guides 124 and, thus, when the guides 124 are fixed to the axial guide 110, the probes can extend a predetermined distance beyond the axial guide 110. The predetermined distance can be selected for particular applications, but in some embodiments can be between greater than zero or one millimeter and about 100 millimeters, preferably between about 10 and about 60 millimeters, and more preferably between about 20 and about 40 millimeters.

The methodology and system of the present invention will reveal the patient's true pelvic axial orientation during the time the surgical implantation operation is being performed. These axial orientation measurements in turn are used as reference points to determine the appropriate angle of inclination angle, as well as the angle of forward flexion of the acetabular implant, such that any existing pelvic tilt may be quickly detected, and that the implanted prosthesis may be properly positioned and oriented into the pelvis in the best possible biomechanical position.

The patient's pelvic axis is properly and accurately reproduced by connecting two identical spots on the pelvis, each on either side of the sagittal plane or midline. The Anterior Superior Iliac Spine (ASIS) is the most prominent bony landmark on the anterior aspect of the pelvis, readily identified with gentle palpation on all patients, regardless of their size, sex, or age.

Figure 5:
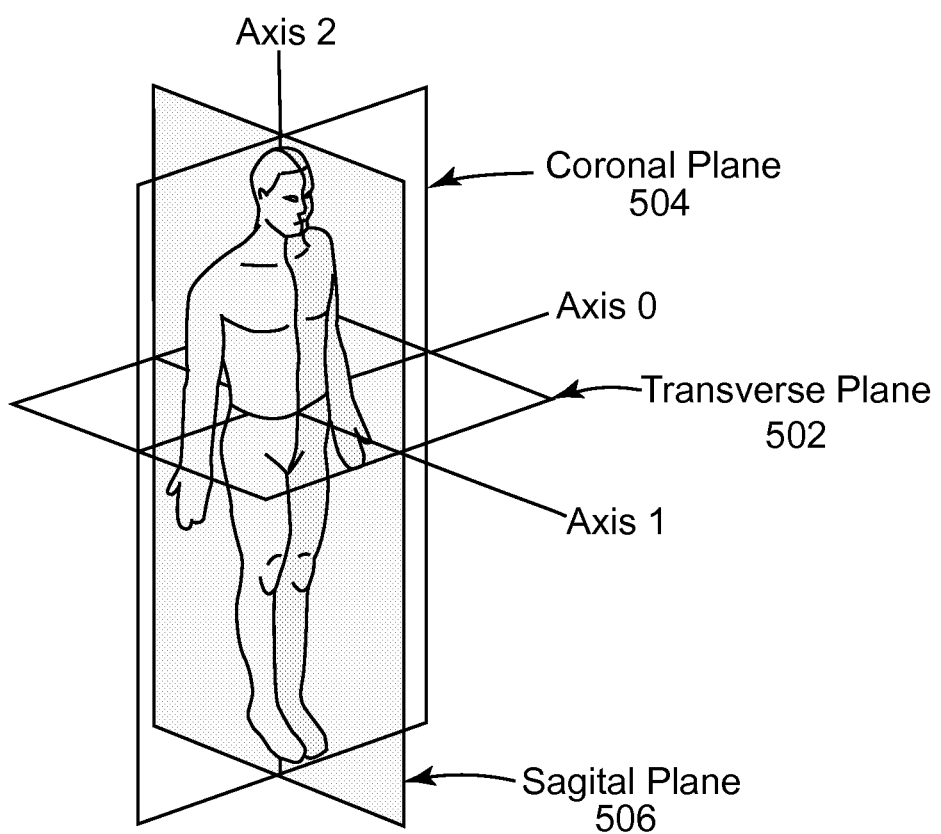
FIG. 5 illustrates various anatomical planes of a patient's body.

The pelvic axis as used herein is defined as follows: The human body is generally divisible by three planes (as shown in FIG. 5), the transverse plane 502 divides the human body into top and bottom sections; the coronal plane 504 divides the body into front (anterior) and back (posterior) portions; and the sagittal plane 506 divides the body into left-sided and right-sided portions. Also by definition and anatomic convention, "Axis 0" is the common line between the transverse and coronal planes; "Axis 1" is the common line between the transverse and sagittal planes; and "Axis 2" is the common line between the coronal and sagittal planes. The pelvic axis is any line defined by the pelvis and generally parallel to Axis 0 or generally perpendicular to the sagittal plane.

When the patient is placed in a supine position, each ASIS can be located by palpation and visibly marked on the skin surface on each side of the pelvis. The pelvic axis is a straight line connecting the right and left ASIS. In one embodiment, the patient's pelvic axis can be physically drawn upon and over the skin surface as a readily visible straight line connecting the right and left ASIS. Note that the pelvic axis should be perpendicular to the midline. A helpful accessory device by which to perform this step accurately and quickly is a laser cross-pointer that is designed or suitable for this particular purpose. In addition, the pre-operative pelvis x-rays should be reviewed in advance by the surgeon for any possible anatomic asymmetry and pelvic obliquity.

The axis guide of choice can be physically placed on the marked spots or pelvic axis line in conformity with and in order to reproduce the patient's pelvis axis. In particular, the axis guide can be placed by centering the slots 112, 114 on either end of the axis guide over the marked right and left ASIS.

In an embodiment using probes 130, incisions can be made in the skin at the location where each guide 124 can be placed. In this way, the probes 130 can be placed directly on the bony pelvis. This approach can be especially useful where the patient's pelvis is covered by tissue that renders it difficult to locate exactly the pelvic axis.

With the guides 124 assembled to the axis guide 110, the probes 130 can be locked into the guides as described above so that each probe extends below the axis guide by a predetermined amount. In this configuration, illustrated in FIG. 3, the assembled axis guide 110 can be thought of as a table having four legs of equal length. While in the illustrated embodiment, the probes each extend an equal amount below the axis guide, there may be anatomies for which having one or more of the probes be a different length may be useful.

The axis guide 110 can be placed over the patient so that the probes 130 extend through the incisions and rest on the patient's bony pelvis. If the patient and axis guide have been prepared properly, the bars 132, 134 of the axis guide will be parallel to the coronal plane of the patient, and thus parallel to the pelvic axis. If this is not the case, the surgeon may move or adjust the orientation of the axis guide so that the bars are parallel to the coronal plane.

With the axis guide 110 in place, one probe 130 on the side of the axis guide on which the surgery will take place can be removed. The guide 124 with the probe removed can now be used, for example, as a guide for driving a self tapping pin (e.g., pin 404 in FIG. 4) into the bony pelvis. In one embodiment, the guide 124 with the probe removed can be used, for example, as a guide for drilling and tapping a hole in the pelvis. With a hole drilled and tapped, a pin may be placed through the guide and engaged to the bone. A typical pin can be threaded, or have some other bone engaging feature on its distal end, and may have a sensor engaging feature on its proximal end. Alternatively, the pin can simple be straight on its proximal end and the sensor 400 can slide over or onto it, as shown in FIG. 4. The pin can be driven into the bone using a manual or power tool.

The second probe 130 on the side of the axis guide on which the surgery will take place can then be removed and replaced with a pin in the same manner as described in the previous paragraph. The axis guide 110 and the remaining probes 130 can then be removed.

The pins so engaged will define a plane that is parallel to the sagittal plane, and thus perpendicular to the pelvic axis. The pins will also be arranged so that each pin extends in a direction that is normal to the coronal plane. The pins can also preferably be engaged to the bone such that their proximal ends are located in a plane that is parallel to the coronal plane. In this configuration, a sensor can be placed on the pins in a known angular relationship with the pelvic axis—the sensor can accurately measure the tilt of the pelvic axis without the need for complicated calibration procedures.

Figure 8:
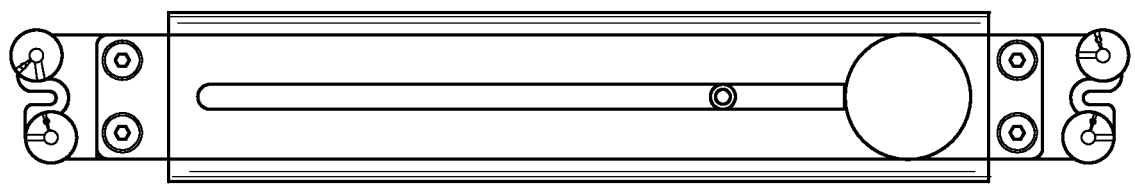
FIG. 8 illustrates a further embodiment of an axis guide.
Figure 9:
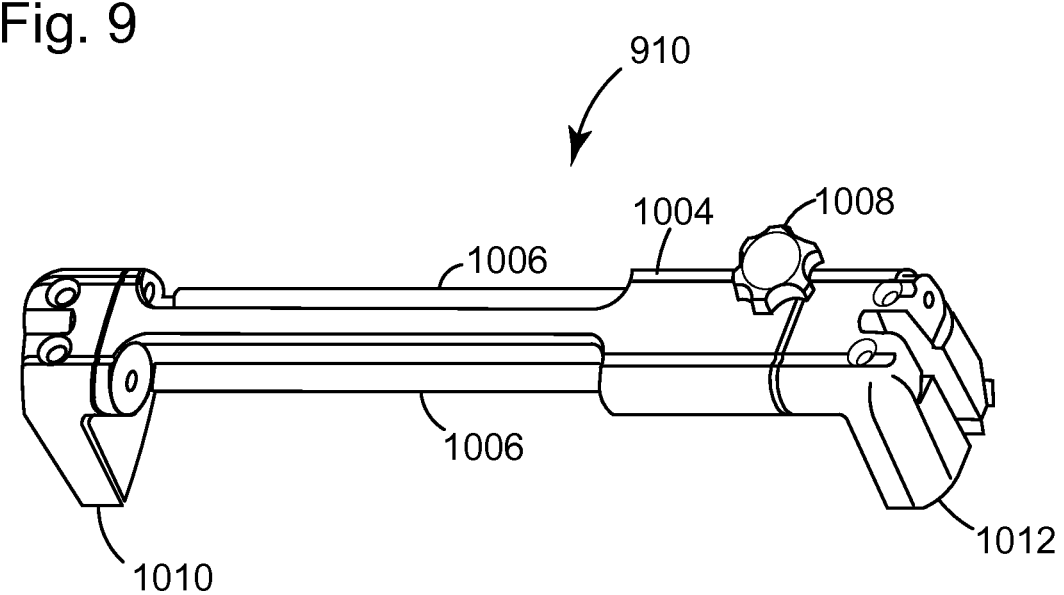
FIG. 9 illustrates another embodiment of an axis guide.
Figure 10:
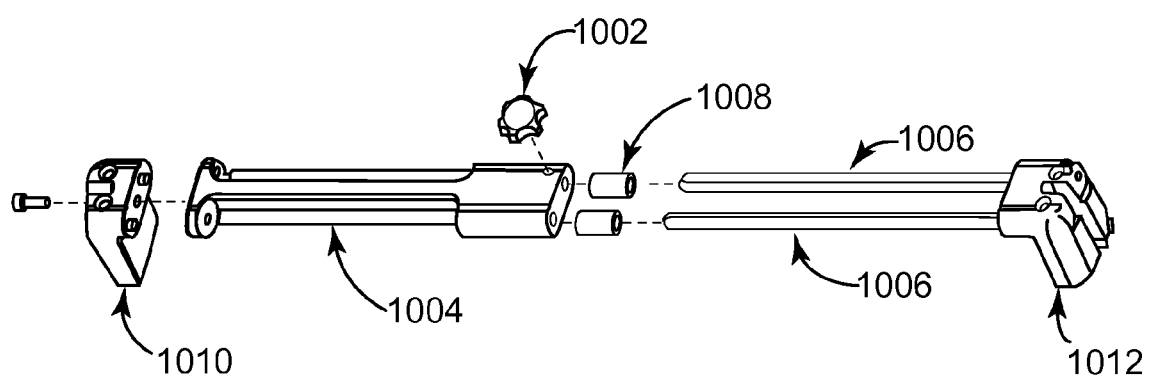
FIG. 10 is an exploded view illustration of the axis guide of FIG. 9.
Figure 11:
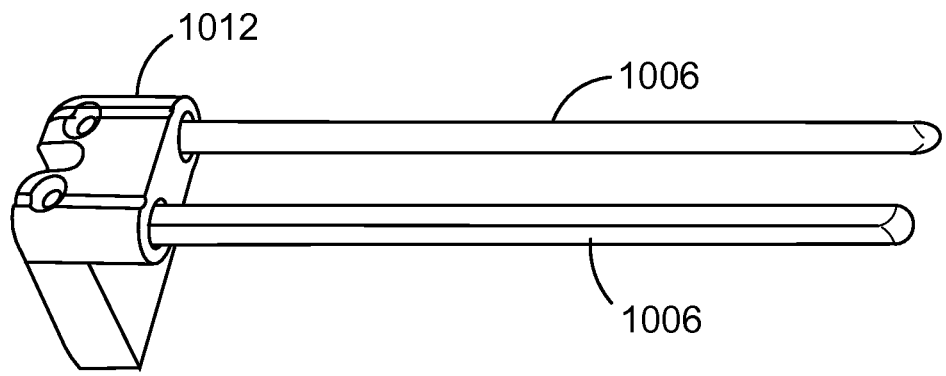
FIG. 11 illustrates the right guide assembly of the axis guide of FIG. 9.
Figure 12:
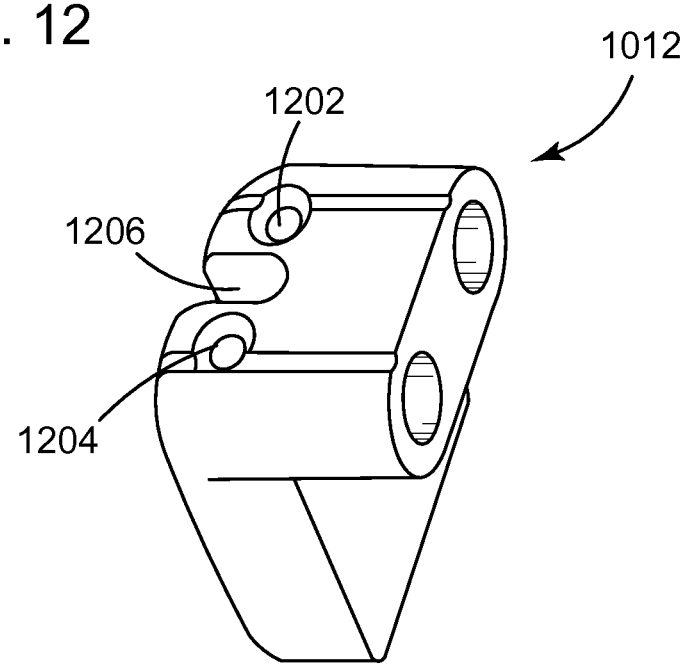
FIG. 12 illustrates the right guide of the axis guide of FIG. 9.
Figure 13A:
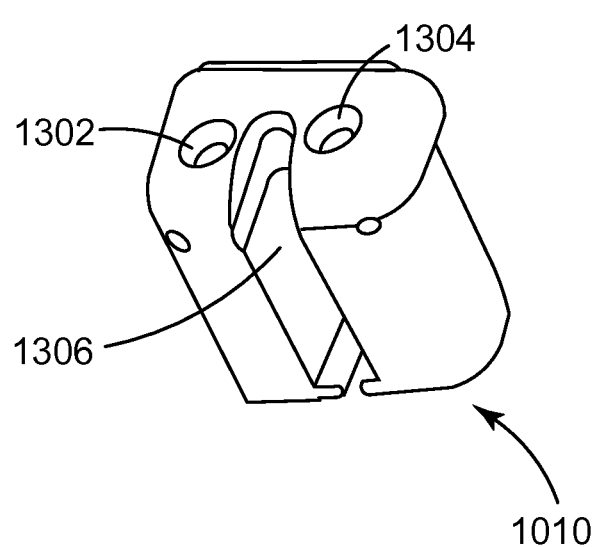
FIGS. 13A and 13B illustrate alternative views of the left guide of the axis guide of FIG. 9.
Figure 13B:
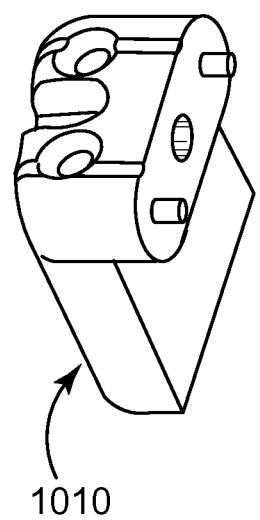
Figure 14:
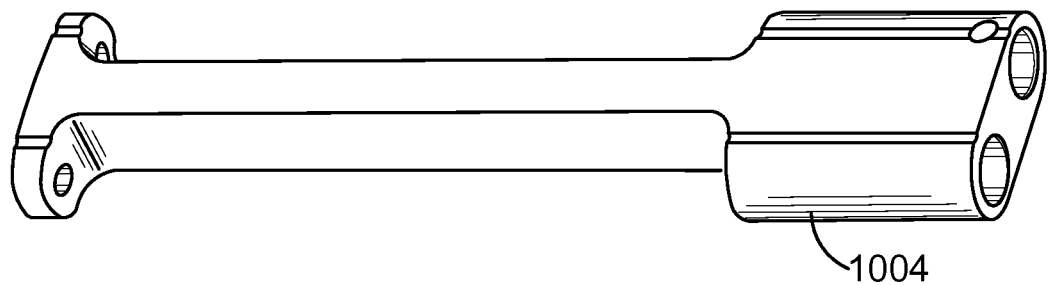
FIG. 14 illustrates the center of the axis guide of FIG. 9.

In embodiment illustrated in FIGS. 1-3, the mating holes 116, 118, 120, 122 for the axis guide can be seen to make out the four corners of a square. In other embodiments, the upper holes 116, 120 shown in FIG. 1 can be moved outward in the medial-lateral direction so that the distance between the upper holes 116, 120 is greater than the distance between the lower holes 118, 122, making the four corners of a trapezoid, as illustrated in FIGS. 6-8. This configuration can allow the pins to be placed on a wider or thicker portion of the patient's pelvis. While this configuration will not result in the pins being aligned with the sagittal plane, it will result in the pins being aligned at a known angle with the sagittal plane. In this case, an offset can be applied to the calculated tilt angles measured by the sensor 400.

Other contemplated variations include providing more or fewer than four guides and/or guide mating holes. For example, a single guide can be provided on the non-surgery side of the axis guide while two guides are provided on the side on which the surgery will be performed. More than four holes and/or guides can also be provided in some embodiments. For example, the axis guide can provide selectable holes in which to place the guides at the selection of the surgeon. By way of further example, holes can be provided in the square configuration noted above, and additional holes can be provided farther apart on the upper side of the axis guide (as also described above)—the surgeon can then select the square configuration, or another configuration based upon a particular patient's anatomy. The probes can also be designed to provide a variable or selectable amount of extension below the axis guide so that the surgeon can adjust the distances based on a particular patient's anatomy.

FIGS. 9-14 illustrate an alternative embodiment of an axis guide 910. Similar to axis guides 110, 210, etc. described above, the axis guide 910 includes components that move relative to one another to allow for adjustment of the overall length of the guide. In the illustrated embodiment, a center portion 1004 can include through-holes to receive shafts 1006 (in certain embodiment, sliding bearing sleeves 1008 can also be included) to allow relative motion. A thumbscrew 1002 can be employed as a locking mechanism to selectively set the overall length of the guide 910. Left and right guides 1010, 1012, respectively, can be coupled to the center portion 1004 and the shafts 1006 to provide properly oriented (i.e., perpendicular to the axis guide 910) through-holes 1202, 1204, 1302, 1304 at each end of the guide 910 for the introduction of probes and/or pins. In the illustrated embodiment, the left and right guides 1010, 1012 can be unitary structures having through-holes formed therein that are configured to permit passage of a probe or pin without allowing radial movement. As a result, the left and right guides can be used without the need for guides 124 and, in some embodiments, can provide greater precision due to the elimination of the threaded connection between the guides 124 and the foot section 254 described above. Of course, the left and right guides 1010, 1012 can include any of the same features as the guides 124, including, e.g., keyhole slot 140, etc., to permit locking a probe in position within the through-holes 1202, 1204, 1302, 1304. Left and right guides 1010, 1012 can also each include a slot 1206, 1306 to provide for centering the axis guide 910 over marked left and right ASIS of a patient.

Figure 15A:
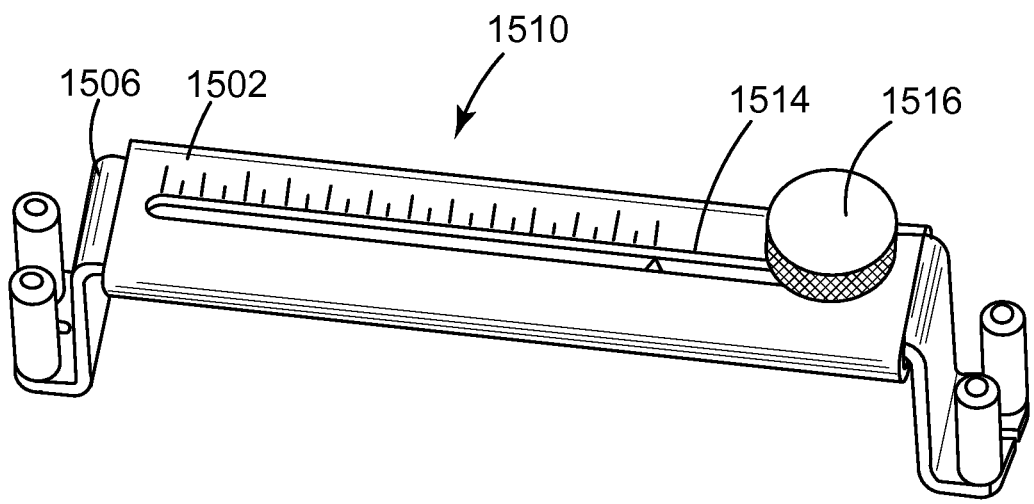
FIGS. 15A and 15B illustrate alternative views of another embodiment of an axis guide.
Figure 15B:
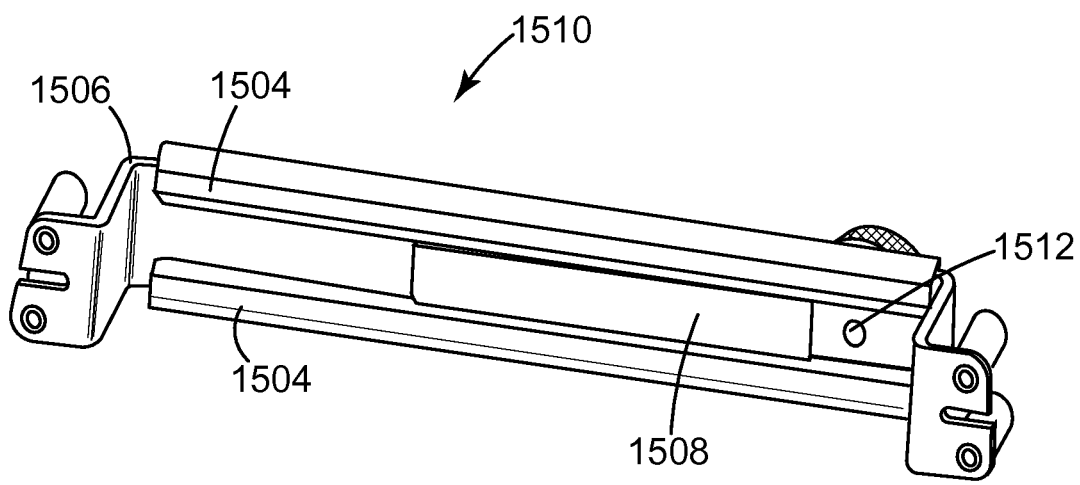

FIGS. 15A and 15B illustrate another embodiment of an axis guide 1510 that is similar to axis guide 210. The guide 1510 can be formed from sheet metal and includes a first rigid bar 1502 that has folded-over ridges 1504 extending along its length. A second rigid bar 1506 can be slidably received between the ridges 1504 along the underside of the first bar 1502. A bearing guide 1508 can be coupled to the underside of the second bar 1506 and sized to fit within the gap between the ridges 1504 so as to prevent misalignment of the guide 1510. Similar to the other embodiments described above, a thumbscrew 1516 can selectively lock the two bars 1502, 1506 by tightening onto a threaded post 1512 that is coupled to the second bar 1506 and extends through the slot 1514 formed in the first bar 1502.

Figure 16A:
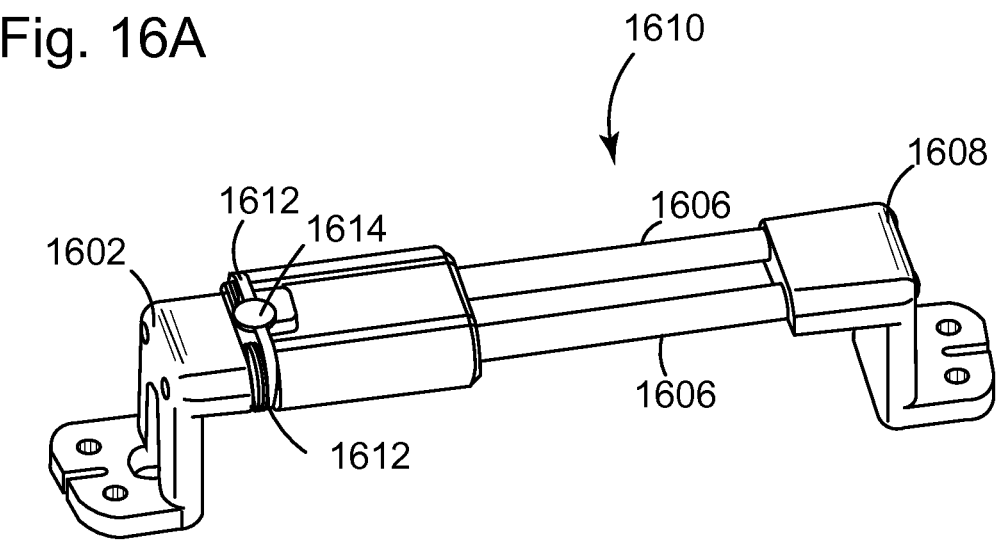
FIGS. 16A and 16B illustrate alternative views of one embodiment of an axis guide.
Figure 16B:
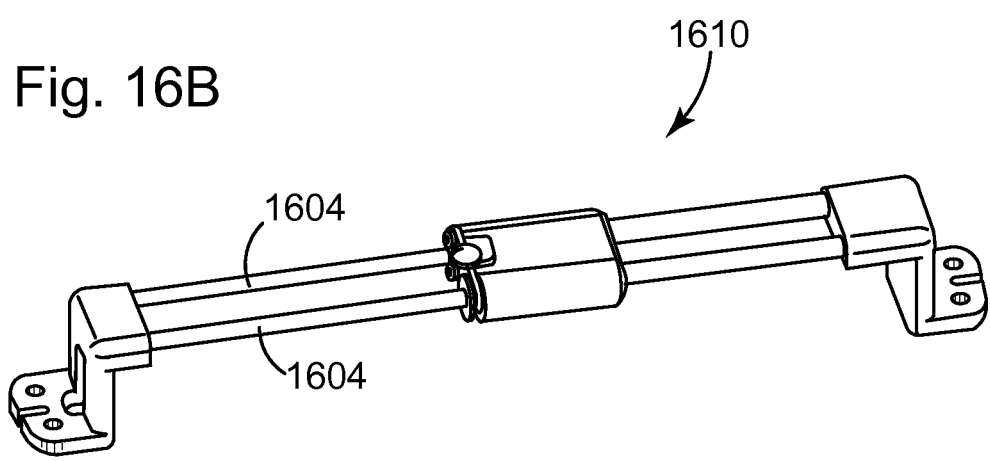

FIGS. 16A and 16B illustrate another embodiment of an axis guide 1610 that allows for adjustment of overall length by providing a left guide 1602 having shafts 1604 coupled thereto that can be received within sleeves 1606 that are, in turn, coupled to a right guide 1608. Further, in the illustrated embodiment quick disconnect fittings 1612 can be provided to allow for one way adjustment, i.e., an overall length of the guide can be increased but not decreased until a release button 1614 is depressed.

Figure 17A:
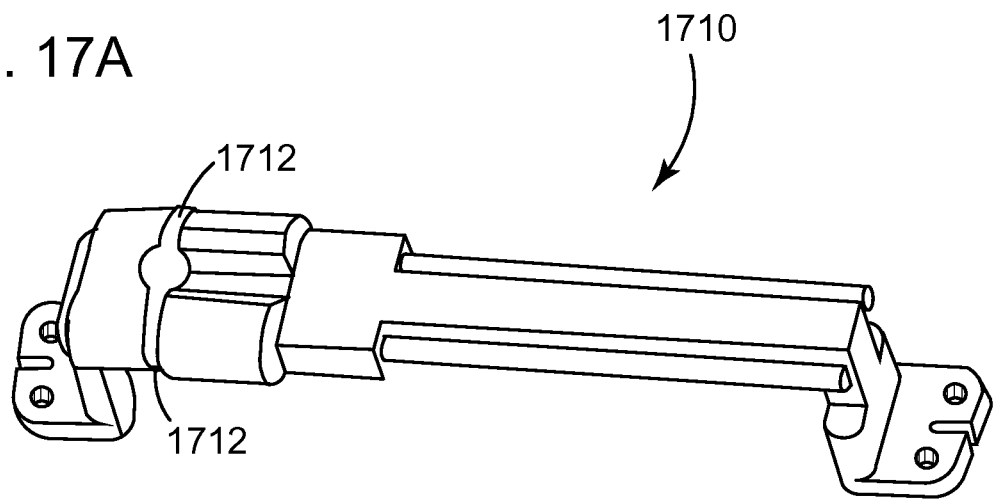
FIGS. 17A and 17B illustrate alternative views of another embodiment of an axis guide.
Figure 17B:
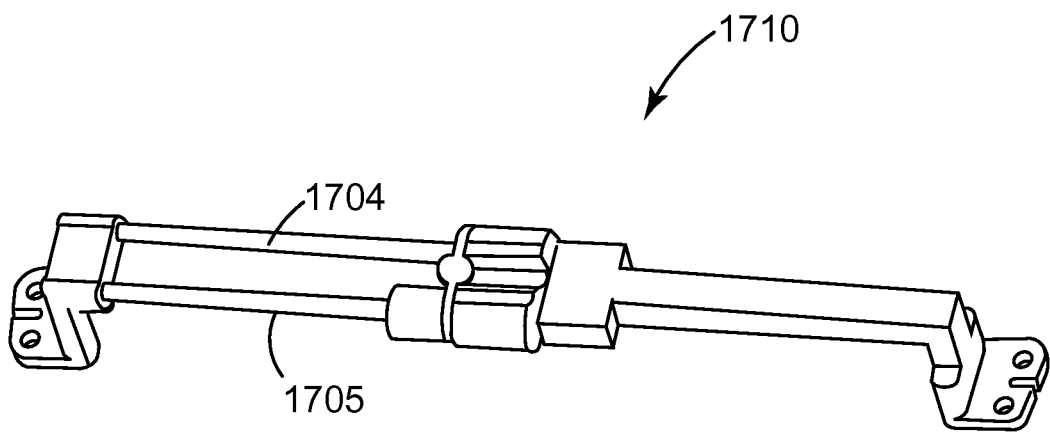

FIGS. 17A and 17B illustrate yet another embodiment of an axis guide 1710 having similar components to the guide 1610. In particular, quick disconnect fittings 1712 can be included to allow for one-way adjustment of the overall length of the guide. Further, in some embodiments quick disconnect fittings on each of shafts 1704, 1705 can be reversed such that a release button must be depressed to allow movement in either direction. In still other embodiments, quick disconnect fittings can be replaced with other mechanisms for preventing motion, such as a thumbscrew or collar clamp.

Figure 18:
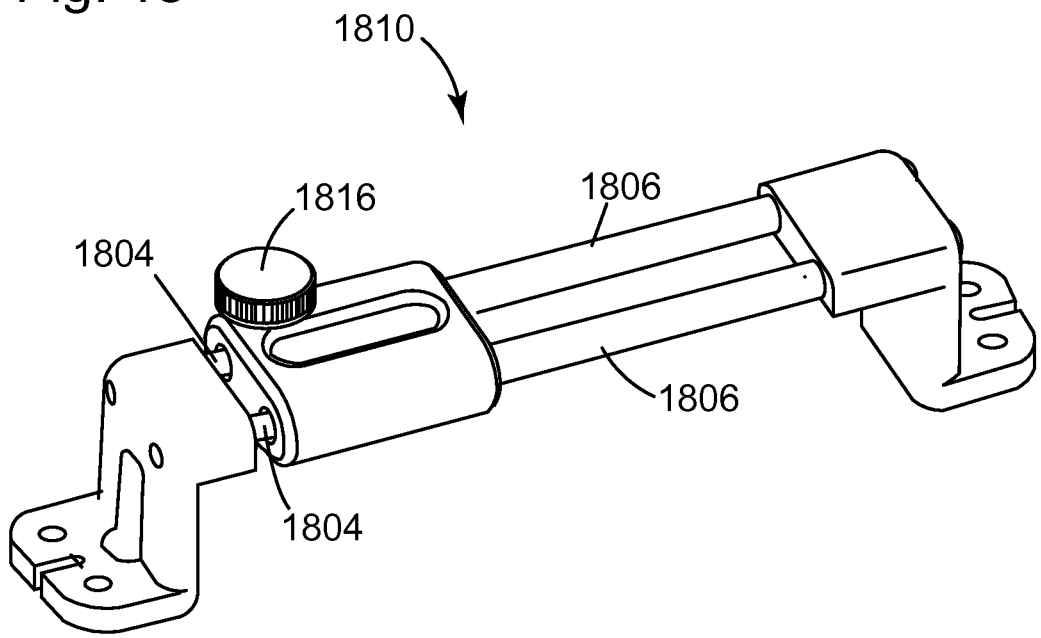
FIG. 18 illustrates one embodiment of an axis guide.
Figure 19:
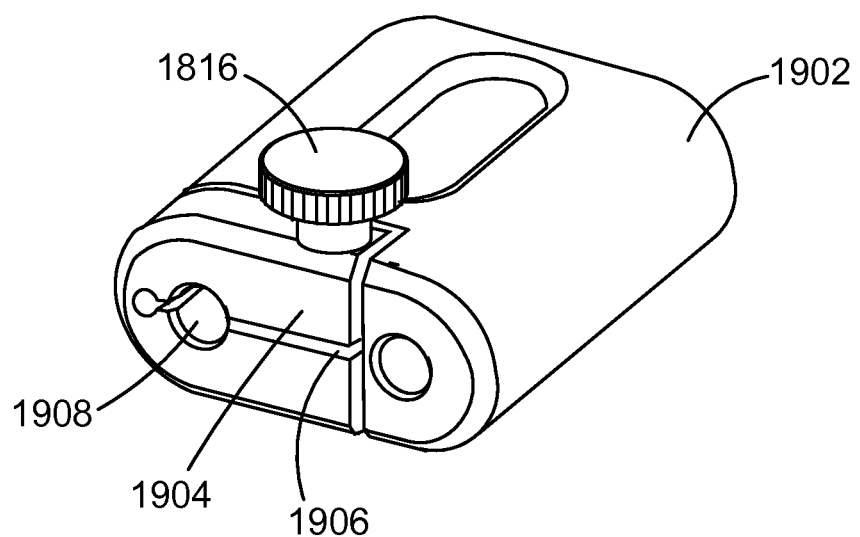
FIG. 19 illustrates a close view of an alternative embodiment of a portion of the axis guide of FIG. 18.

FIG. 18 illustrates an alternative embodiment of a axis guide 1810 that includes a similar configuration of inner shafts 1804 and outer sleeves 1806. A thumbscrew 1816 can be used to prevent relative motion between the shafts 1804 and sleeves 1806. In a case where a set screw may mar or otherwise harm a finish on the shaft 1804, an alternative design shown in FIG. 19 can be employed. In the illustrated design, the thumbscrew 1816 threads into a floating portion 1904 of the block 1902 to close the gap 1906 formed in the block and thereby reduce the diameter of the through-hole 1908 formed in the block. The reduction in diameter of the through hole 1908 can clamp down on the shaft 1804 evenly around a circumference thereof and prevent adjustment of the length of the axis guide.

Figure 20:
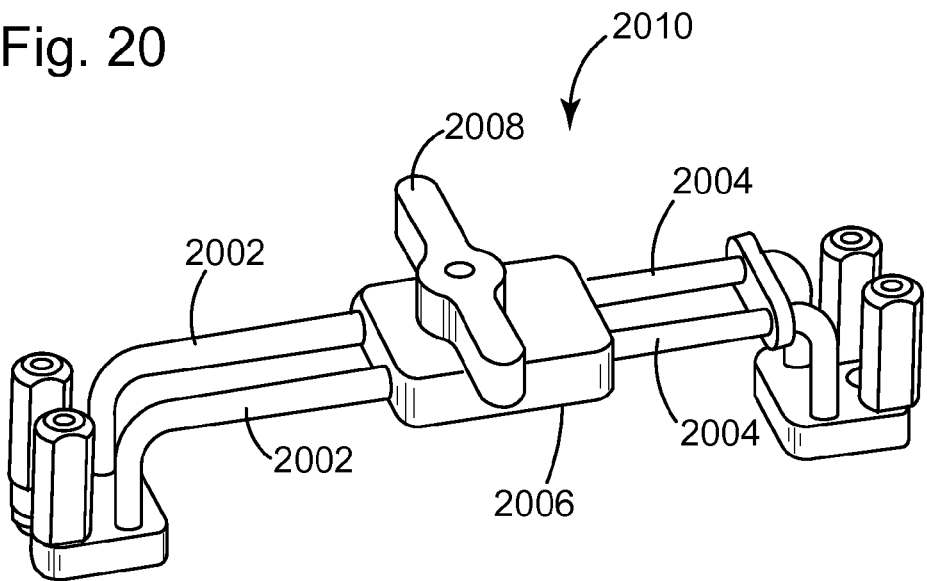
FIG. 20 illustrates one embodiment of an axis guide.
Figure 21:
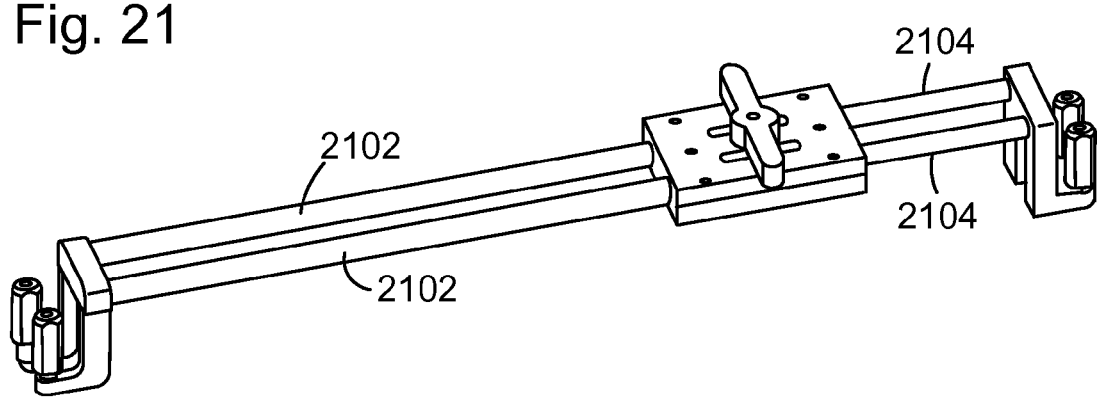
FIG. 21 illustrates another embodiment of an axis guide.

FIG. 20 illustrates an alternative embodiment of an axis guide 2010 in which bent tubes 2002, 2004 telescope into one another to allow adjustment of the overall length of the guide. A center portion 2006 can include a locking mechanism 2008 to selectively lock the guide at a desired length. FIG. 21 illustrates an alternative embodiment of an axis guide 2110 that is similar to the guide 2010, but utilizes straight tubes 2102, 2104.

Figure 22:
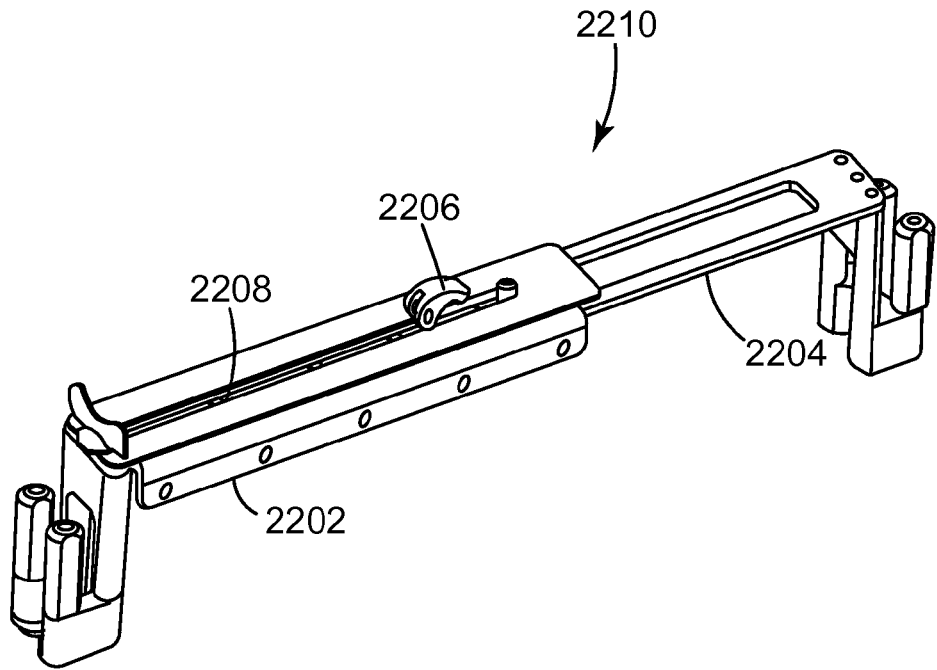
FIG. 22 illustrates still another embodiment of an axis guide.

FIG. 22 illustrates another embodiment of an axis guide 2210 that can be formed from sheet metal components and includes first and second rigid bars 2202, 2204, similar to other embodiments described herein. The first bar 2202 can include folded-over edges to maintain alignment of the bars 2202, 2204 after assembly. A latch 2206 can be coupled to the second bar 2204 and configured to protrude through a slot 2208 formed in the first bar 2202. The latch can be configured to compress the two bars 2202, 2204 together upon actuation, thereby preventing relative motion therebetween.

Figure 23:
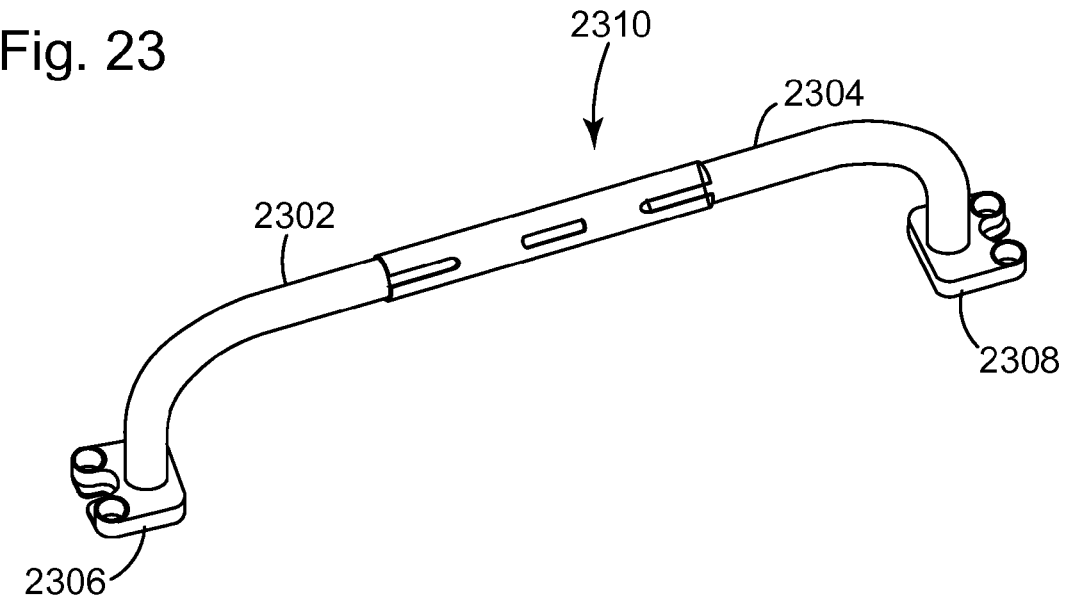
FIG. 23 illustrates one embodiment of an axis guide.
Figure 24:
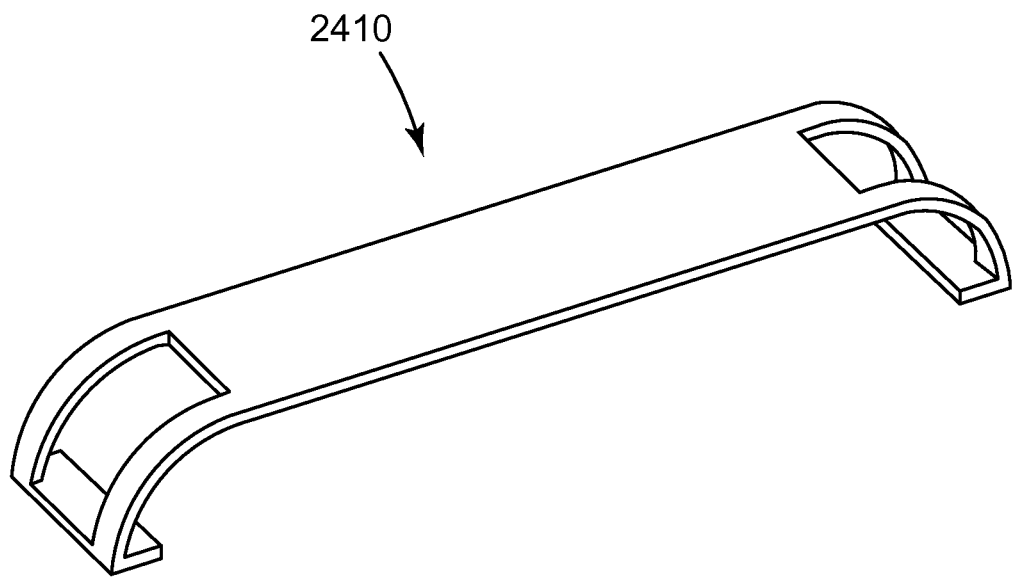
FIG. 24 illustrates another embodiment of an axis guide.

FIGS. 23 and 24 illustrate still other embodiments of axis guides 2310, 2410. These simple designs utilize telescoping tubes 2302, 2304 or sliding sheet metal (or other material) components, similar to other embodiments described above. In the case of the axis guide 2310 that employs a single set of telescoping tubes 2302, 2304, features to prevent relative rotation can be provided. For example, a slot can be formed in the tube 2304 that is configured to receive a protrusion formed on an outer surface of the tube 2302. Such a feature can ensure that the left and right guides 2306, 2308 remain parallel to one another.

Regardless of the embodiment of axis guide utilized, after pins are attached to a patient's pelvis and a sensor (e.g., sensor 400) affixed thereto, tilt angles reported by the sensor can be reported on a graphical user interface, such as display 402 shown in FIG. 4. That interface can report on the anterior-posterior (AP) and/or axial tilt of the pelvis. It can also provide a graphic showing the orientation of the patient's pelvis. If the surgeon wishes to have the patient's pelvis oriented differently for surgery, changes to the patient's position may be made with real time monitoring of the orientation of the pelvis.

The devices disclosed herein can be designed for multiple uses and can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the devices described herein will be processed before surgery. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. In other embodiments, sterilization can be performed using any number of ways known to those skilled in the art including beta or gamma radiation, ethylene oxide, steam, or a liquid bath (e.g., cold soak).

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A system for providing pins in a patient's pelvis for attaching an orientation sensor in a known relationship to the patient's pelvic axis, the system comprising:
   an axis guide for placement over a patient's right and left ASIS having a surgical side and a non-surgical side, the surgical side including at least two guide mating holes;
   at least two guides attachable to the guide mating holes so as to provide a through hole that is perpendicular to the axis guide;
   at least two probes, each probe fitting through the through holes and having a locking feature that engages a feature on the guides that locks the axial position of the probe so that it extends by a predetermined distance beyond the end of the axis guide when assembled; and
   at least two bone engaging pins, each bone engaging pin fitting through the through holes and having a bone engaging feature on its distal end;
   wherein when the guides are assembled to the axis guide and the probes are assembled to the guides, and the axis guide is placed so that the probes contact the patient's pelvis, the probes can be replaced by the pins so as to mount the pins to the patient's pelvis in a direction that is normal to the patient's coronal plane.

2. The system of claim 1, wherein the non surgical side of the axis guide includes two guide mating holes, and the system includes two further guides and two further probes.

3. The system of claim 2, wherein the probes extend beyond the axis guide by between 10 and 60 millimeters when the guides are assembled to the axis guide and the probes are assembled to the guides.

4. The system of claim 2, wherein the guide mating holes are arranged in a square pattern.

5. The system of claim 1, wherein the axis guide includes a plurality of selectable guide mating holes for placement of a single guide.

6. The system of claim 1, further comprising a tilt sensor mountable to the pins in a known orientation with respect to the patient's pelvic axis.

7. The system of claim 6, the tilt sensor includes a transmission element and the system further comprises a computing device having a graphical user interface that provides visual guidance as to the orientation of the patient's pelvic axis.

8. A system for providing pins in a patient's pelvis for attaching an orientation sensor in a known relationship to the patient's pelvic axis, the system comprising:
   an axis guide for placement over a patient's right and left ASIS having a surgical side and a non-surgical side, the surgical side including at least two guide holes that are perpendicular to the axis guide;
   at least two probes, each probe fitting through the guide holes and having a locking feature that engages a feature on the axis guide that locks the axial position of the probe so that it extends by a predetermined distance beyond the end of the axis guide when assembled; and
   at least two bone engaging pins, each bone engaging pin fitting through the guide holes and having a bone engaging feature on its distal end;
   wherein when the probes are assembled to the axis guide, and the axis guide is placed so that the probes contact the patient's pelvis, the probes can be replaced by the pins so as to mount the pins to the patient's pelvis in a direction that is normal to the patient's coronal plane.

* * * * *